United States Patent [19]

Rizkalla

[11] 4,323,697

[45] Apr. 6, 1982

[54] PROCESS FOR PREPARING ETHYLIDENE DIACETATE

[75] Inventor: Nabil Rizkalla, River Vale, N.J.

[73] Assignee: The Halcon SD Group, Inc., New York, N.Y.

[21] Appl. No.: 219,787

[22] Filed: Dec. 24, 1980

[51] Int. Cl.$^3$ .................... C07C 67/36; C07C 67/37; C07C 69/16
[52] U.S. Cl. .................................. 560/232; 260/546; 260/549; 560/263; 562/517; 568/484; 568/485
[58] Field of Search ............................... 560/232, 263

[56] References Cited

FOREIGN PATENT DOCUMENTS 1538782 1/1979 United Kingdom ................ 560/263

Primary Examiner—Vivian Garner
Attorney, Agent, or Firm—William C. Long; David Dick; Riggs T. Stewart

[57] ABSTRACT

Ethylidene diacetate is prepared by treating methyl acetate and/or dimethyl ether with carbon monoxide and hydrogen by the use of a molybdenum-nickel or tungsten-nickel co-catalyst, in the presence of an iodide and in the presence of a promoter comprising an organo-phosphorus compound or an organo-nitrogen compound wherein the phosphorus and nitrogen are trivalent and in the presence of an iodide.

4 Claims, No Drawings

PROCESS FOR PREPARING ETHYLIDENE DIACETATE

This invention relates to the preparation of ethylidene diacetate and is more particularly concerned with the preparation of this ester from methyl acetate and/or dimethyl ether.

Ethylidene diacetate is a chemical intermediate of prime commercial interest in view of its ready convertibility to a number of different tonnage chemicals of commerce. By one known conversion technique, ethylidene diacetate is readily transformed to vinyl acetate plus acetic acid; see Kirk-Othmer "*Encyclopedia of Chemical Technology,*" (2nd ed.), vol. 21, page 321, Interscience, New York (1970). By another well-known conversion process, ethylidene diacetate can be transformed into acetic anhydride plus acetaldehyde; see Kirk-Othmer "*Encyclopedia of Chemical Technology,*" (2nd ed.), vol. 8, pages 410–413, Interscience, New York (1965). Reference is also made to U.S. Pat. No. 2,425,389 as indicative of the flexibility of ethylidene diacetate as a chemical intermediate.

Various processes have been proposed for the preparation of ethylidene diacetate. One such process involves the reaction of acetaldehyde and acetic anhydride, the ethylidene diacetate being produced as an intermediate in the preparation of vinyl acetate, a process which has been employed to a limited extent on a commercial scale; see "Hydrocarbon Process" 44 (11), 287 (1965). Fenton U.S. Pat. No. 3,579,566 treats organic acid anhydrides such as acetic anhydride with hydrogen in the presence of a catalyst comprising a complex of a Group VIII noble metal with a biphyllic ligand from the group consisting of trihydrocarbyl phosphines, arsines and stibines. The Fenton examples show the preparation of ethylidene diacetate from acetic anhydride by this technique.

Belgian Pat. No. 879,178 also produces ethylidene diacetate by the process described by Fenton but uses a heterogenous reaction system with supported metal catalysts or catalysts in the zero valent state. British Pat. No. 1,538,782 discloses another technique for producing ethylidene diacetate which employs the carbonylation of methyl acetate or dimethyl ether in the presence of hydrogen by means of Group VIII noble metal catalysts.

The Group VIII noble metals, i.e., ruthenium, rhodium, palladium, osmium, iridium and platinum are, however, relatively expensive metals but their use has heretofore been considered essential in the preparation of ethylidene diacetate from methyl acetate and/or dimethyl ether.

It is accordingly an object of this invention to provide an improved process for the preparation of ethylidene diacetate.

It is a further object of the invention to provide an improved process for the preparation of ethylidene diacetate from methyl acetate and/or dimethyl ether which does not require the use of Group VIII noble metals as catalysts.

In accordance with the invention, these and other objects are realized by the reaction of methyl acetate and/or dimethyl ether with hydrogen and carbon monoxide by using a molybdenum-nickel or a tungsten-nickel co-catalyst in the presence of a promoter comprising an organo-phosphorus compound or an organo-nitrogen compound wherein the phosphorus and nitrogen are trivalent, and in the presence of an iodide. It has been discovered that this co-catalyst in combination with the promoter iodide system of the character indicated makes possible, without the use of a Group VIII noble metal, the conversion of methyl acetate and/or dimethyl ether to ethylidene diacetate in high yields.

Thus, in accordance with the invention, the ester ethylidene diacetate can be effectively prepared in a representative case by subjecting methyl acetate and/or dimethyl ether to reaction with hydrogen and carbon monoxide in the presence of methyl iodide and in the presence of the co-catalyst-promoter-system described above. In all cases, the reaction is carried out under anhydrous conditions.

The process of this invention can be carried out in the vapor or liquid phase, with liquid-phase operation being preferred. In vapor-phase operation, the carbon monoxide, hydrogen and methyl acetate (and/or dimethyl ether) together with the source of halide are introduced for contact with the co-catalyst and promoter within the reaction zone. In the liquid-phase embodiment, the carbon monoxide, hydrogen and methyl acetate (and/or dimethyl ether) reactants are contacted with a liquid-phase reaction medium containing the co-catalyst and promoter within the reaction zone and maintained in contact therewith for a time sufficient to permit reaction to occur. In this preferred (liquid-phase) embodiment, the source of halide can be a component of the liquid-phase reaction medium and need not be introduced together with the reactants. A portion of the liquid-phase reaction medium, now containing ethylidene diacetate, can then be withdrawn from the reaction zone and processed for the recovery of ethylidene diacetate. The ethylidene diacetate can then be marketed as such or can be converted to acetaldehyde plus acetic anhydride and/or to vinyl acetate plus acetic acid.

The over-all reaction that appears to occur when methyl acetate is employed as the reactant can be expressed by the following chemical equation:

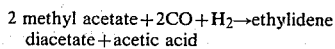

$$2 \text{ methyl acetate} + 2CO + H_2 \rightarrow \text{ethylidene diacetate} + \text{acetic acid}$$

When dimethyl ether is used as the reactant in lieu of methyl acetate, the overall reaction is slightly different and can be expressed by the following chemical equation:

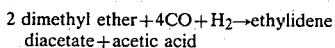

$$2 \text{ dimethyl ether} + 4CO + H_2 \rightarrow \text{ethylidene diacetate} + \text{acetic acid}$$

Mixtures of methyl acetate and dimethyl ether can, of course, be used. Further, although the foregoing equations indicate acetic acid as a primary reaction co-product, other co-products are often obtained instead of or in addition to acetic acid. The primary co-products often observed are acetic anhydride and/or acetaldehyde. The nature and distribution of these co-products depends in large measure upon the ratio of carbon monoxide to hydrogen employed, as hereinafter discussed. Formation of ethanol or other ethyl derivatives, however, is not noted to occur to a significant extent, though these may be formed in trace amounts.

The acetic acid co-product of the overall carbonylation reaction is readily recovered as, for example, by distillation techniques, and can be purified for use as such and/or can be reacted with methanol to produce the methyl acetate reactant. Purification of the co-product acetic acid obtained in this process is readily effected since, because the reaction medium is anhydrous, water removal is not required to achieve concentrations approaching glacial. When the acetic acid is recycled for use in preparing additional methyl acetate, the overall effect can, in practice, result in a no co-product ethylidene diacetate production process.

Further, since methanol itself can be readily converted to dimethyl ether and/or methyl acetate by known techniques, the process of this invention provides a technique for the conversion of methanol to ethylidene diacetate. And since methanol need not be obtained from petroleum-based materials, the advantages of this process over currently prevailing techniques for production of any one or more of acetic anhydride, acetaldehyde, vinyl acetate, and acetic acid becomes readily apparent.

When using dimethyl ether as the organic raw material (in addition, of course, to carbon monoxide and hydrogen), it is believed (but not confirmed) that the initial step involved is the carbonylation of the ether to produce methyl acetate. Thus, although dimethyl ether can readily be employed as a raw material for use in the process of this invention, the use of methyl acetate (alone or in admixture with dimethyl ether) is particularly preferred, especially methyl acetate alone.

When dimethyl ether is employed as the starting material for the process of this invention, the reaction can be carried out in one or more reaction zones. Thus, in this embodiment, a preferred procedure would involve the use of two reaction zones, in the first of which dimethyl ether would be converted by carbonylation to methyl acetate, with the second reaction zone being devoted to the conduct of the ethylidene diacetate-forming reaction. In this fashion differing reaction conditions can be employed for (a) the conversion of dimethyl ether to methyl acetate and (b) the conversion of methyl acetate to ethylidene diacetate so that each of the two reaction zones may be maintained under optimum conditions for the reactions conducted therein.

However, the use of separate reaction zones is not necessary because the conversion of dimethyl ether to methyl acetate can be carried out concurrently with and in the same reaction zone as that in which the ethylidene diacetate is formed.

Aside from the dimethyl ether and/or methyl acetate reactants, necessary reactants for the production of the ethylidene product are carbon monoxide and hydrogen. These can be introduced to the reaction zone (or zones) either together or separately. In vapor phase operation, it is, of course, also necessary to introduce the source of halide together with the reactants, again either together with or separately from the reactants.

It will be noted that while hydrogen is a necessary co-reactant with carbon monoxide for the production of ethylidene diacetate, it is not a necessary co-reactant for the conversion of dimethyl ether to methyl acetate. Assuming for convenience that carbon monoxide and hydrogen are separately introduced to the reaction zone wherein ethylidene diacetate is produced, each is preferably employed in substantially pure form, as available commercially. In each case, however, inert diluents such as carbon dioxide, nitrogen, methane, and/or inert gases (e.g., helium, argon, neon, etc.) can be present if desired. The presence of inert diluents of these types does not affect the desired carbonylation reactions, but their presence makes it necessary to increase the total pressure in order to maintain the desired carbon monoxide and hydrogen partial pressures.

All reactants (i.e., carbon monoxide, hydrogen, as well as the methyl acetate and/or dimethyl ether) should be substantially free from water since, in this fashion, the maintenance of a substantially anhydrous condition within the reaction zone is facilitated. The presence of minor amounts of water, however, such as may be found in these commercially available reactants, is permissible. Normally, however, the presence of more than 5 mol % of water in any one or more of the reactants should be avoided, the presence of less than 3 mol % of water is desired, and the presence of less than 1.0 mol % of water is preferred. The presence of the conventional organic impurities found in commercial grades of dimethyl ether and/or methyl acetate, however, pose no problem to the practice of this invention.

As hereinabove indicated, preferred practice calls for conduct of the instant reaction in the liquid phase in the presence of a substantially anhydrous liquid-phase reaction medium. Since water is not a product of the reaction, maintenance of substantially anhydrous conditions within the liquid-phase reaction medium is simply accomplished by insuring adequate dryness and freedom from alcoholic hydroxyl groups (i.e., free alcohol) of the necessary reactants and/or recycle streams introduced to the reaction zone. The liquid-phase reaction medium thus contains reactants (carbon monoxide, hydrogen, dimethyl ether, and/or methyl acetate), reaction products (ethylidene diacetate, and acetic anhydride), as well as the halide and catalyst necessary for the conduct of the desired reaction, together with such co-products as may be formed, including usually acetaldehyde and/or acetic anhydride.

To facilitate conduct of the reaction in the liquid phase, solvents or diluents can be employed. The solvents or diluents are preferably materials which are indigenous to the reaction system such as, for example, excess dimethyl ether and methyl acetate and/or methyl halide and/or acetyl halide (preferred halide sources), and/or co-products commonly found in the reaction system, such as acetic acid, acetaldehyde, and/or acetic anhydride. Excess dimethyl ether and/or methyl acetate are the preferred reaction diluents, with acetic acid and/or acetic anhydride being the preferred alternates.

It is also practicable to employ organic solvents or diluents which are inert in the environment of the process. The most suitable inert solvents or diluents are hydrocarbons free from olefinic unsaturation, typically the paraffinic, cycloparaffinic, and aromatic hydrocarbons such as octane, benzene, toluene, the xylenes, cyclododecane, and the like. Other suitable solvents include chloroform, carbon tetrachloride, and acetone. When such non-indigenous solvents or diluents are employed, they are preferably selected so that the solvent or diluent has a boiling point sufficiently different from the components of the reaction mixture to facilitate the separation of the components of the reaction mixture from the solvent or diluent.

Also as hereinbefore indicated, the reaction requires the presence of an iodide which, in the preferred liquid-phase mode of operation, would be a component of the liquid-phase medium. The iodide would usually be present largely in the form of methyl iodide, acetyl iodide, hydrogen iodide, or mixtures of the foregoing species, and could be introduced to the liquid phase reaction medium as such. However, it is entirely sufficient, particularly in batch operation, to charge materials to the liquid phase such that any one or more of these materials (i.e., methyl iodide, acetyl iodide, and/or hydrogen iodide) are formed in situ. Materials which interact in situ with the other components of the liquid phase reaction medium to form methyl iodide, acetyl iodide, and/or hydrogen iodide include inorganic iodide materials, e.g., salts such as the alkali metal and alkaline earth metal salts, as well as elemental iodine and the like. In continuous operation, wherein reaction by-products are separated (as for example, by distillation and/or extraction techniques), and recycled to the reaction medium, organic iodides such as methyl iodide and/or acetyl iodide will be present as components of the liquid phase reaction medium and can be recovered and recycled to the reaction zone as such; thus, only a small quantity of make-up halide need be supplied to compensate for such losses in recovery as may be encountered.

The amount of iodide component may vary widely but, in general, it should be present in an amount of at least 10 mols (expressed as I) per hundred mols of ester or ether. Typically, 10 to 50 mols of the iodide per 100 mols of ester or ether, preferably 17 to 35 mols per 100 mols. Ordinarily, more than 200 mols of iodide per 100 mols of ester or ether are not used. The iodide component, however, does not have to be added as a hydrocarbyl iodide but can be supplied as another organic iodide or as the hydroiodide or other inorganic iodide, e.g., a salt such as the alkali metal or other metal salt, or even as elemental iodine.

In typical practice the liquid-phase reaction medium, neglecting water and non-indigenous solvents or diluents employed, would normally contain the following materials within the following concentration ranges, expressed on a mol % basis unless otherwise indicated:

| | |
|---|---|
| Halide, wt. % (contained basis) | 0.1–75% |
| Acetaldehyde | 0–40% |
| Acetic acid | 1–75% |
| Acetic anhydride | 0–80% |
| Ethylidene diacetate | 1–60% |
| Dimethyl ether | 0–50% |
| Methyl acetate | 5–90% |

When non-indigenous solvents are employed, they would normally comprise from 5 wt. % to 95 wt. %, desirably from 10 wt. %, and preferably from 15 wt. % to 80 wt. % of the liquid-phase reaction medium.

Not included in the foregoing tabulation are the quantities of dissolved carbon monoxide and hydrogen necessarily present within the liquid-phase reaction medium in order to permit the desired reaction or reactions to occur.

It will be noted that liquid-phase reaction media within the foregoing concentration ranges are readily processible in order to recover ethylidene diacetate therefrom because of the wide difference in volatilities associated with these materials. Methyl halides are generally highly volatile materials. These can thus be readily separated by distillation and/or extraction techniques for recovery and recycle to the reaction zone. Any acetic acid and acetic anhydride present in the system can readily be recovered. Ethylidene diacetate, however, is of substantially lesser volatility and can accordingly readily be recovered in whatever degree of purity may be desired. Inert solvents or diluents, if present, can readily be chosen from the standpoint of volatility characteristics to facilitate their recovery and re-use.

As indicated, the process of this invention preferably occurs in the presence of a liquid-phase reaction medium confined within a reaction zone. A single reaction zone or a plurality of reaction zones in series or in parallel may be employed. The process itself can be carried out in batch, semi-continuous or continuous manner. The reaction zone itself may comprise one or more autoclaves or an elongated tubular zone or series of such zones. The reaction zone is suitably fitted with internal and/or external heat-removal devices to absorb the exothermic heat of reaction and facilitate maintenance of proper temperature control during the course of the reaction. Suitably, the reaction zone is configured to provide sufficient agitation to insure adequate contact between the carbon monoxide and hydrogen reactants and the ether-acetate reactants. Any convenient agitation means known to those skilled in the art may be used, including vibration, shaking, stirring, etc., as illustrative techniques. Normally the reactants would be introduced at a point within the reaction zone below the level of the liquid phase reaction medium maintained therewithin in order to facilitate agitation and adequate contact by gas-sparging techniques.

The process of this invention can be carried out over a wide range of temperatures. Temperatures, for example, from 20°–500° C. are suitable, with temperatures of 80°–350° C. being preferred and temperatures of 100°–250° C. being most preferred. Temperatures lower than those mentioned can be used but they tend to lead to reduced reaction rates. Higher temperatures than those mentioned can be employed, but there is no particular advantage to such practice.

Reaction time is not a significant parameter of the process of this invention, depending to a large extent upon the temperature employed as well as upon reactant concentrations. Suitable reaction times (i.e., times sufficient for the ethylidene diacetate-forming reaction to occur) for liquid-phase embodiments will normally be within the range of 0.05 to 20 hours, more generally 1 to 10 hours.

For the preferred liquid-phase embodiments, reaction total pressure also is an unimportant process parameter so long as it is sufficient to maintain the liquid-phase reaction medium and the appropriate carbon monoxide and hydrogen partial pressures. Suitable carbon monoxide and hydrogen partial pressures are each preferably within the range of 5–5,000 psi, most preferably within the range of 25–3,000 psi. Broader partial pressure ranges, however, can be employed, within the ranges from 0.1 to 15,000 psi being applicable. While yet higher partial pressures can be employed, there is little advantage to their use and a substantial economic penalty would be incurred as a result of building equipment capable of withstanding such higher pressures.

The stoichiometry of the chemical equations set forth above suggests that the reaction resulting in the formation of ethylidene diacetate would require a molar ratio of carbon monoxide to hydrogen varying rom 2:1 to 4:1, depending upon whether dimethyl ether or methyl acetate (or mixtures thereof) was employed. It has, however, been found that much broader molar ratios of carbon monoxide to hydrogen, broadly within the range of 1:100 to 100:1, desirably within the range of 50:1 to 1:50, and preferably within the range of 10:1 to 1:10 can be employed. Best results are obtained with carbon monoxide-hydrogen mixtures which approach the stoichiometric ratios of carbon monoxide to hydrogen. Molar ratios of carbon monoxide to hydrogen within the range of 0.5:1 to 5:1 are thus an especially preferred regime of operation.

The molar ratio of carbon monoxide to hydrogen also affects the nature of the co-products obtained. The foregoing equations indicate that acetic acid is the co-product formed. Other co-products can, however, be made, especially acetic anhydride and acetaldehyde. For example, other conditions remaining constant in a liquid-phase system, increasing the molar ratio of carbon monoxide to hydrogen increases the molar ratio of acetic anhydride to acetic acid produced. Conversely, reducing the molar ratio of carbon monoxide to hydrogen increases the molar ratio of acetaldehyde to acetic acid produced. Thus, the process of this invention provides a considerable degree of flexibility in the distribution of co-products obtainable.

For liquid-phase operation, the molar ratios of carbon monoxide plus hydrogen to dimethyl ether and/or methyl acetate employed are dictated by the partial pressure criteria set forth above, since partial pressure and liquid-phase concentrations of these normally gaseous reactants are directly interrelated.

Once the reaction has been carried out, the reaction effluent is withdrawn from the reaction zone and introduced into a distillation zone which can comprise one or a series of distillation columns. In these columns, ethylidene diacetate and co-product acetic acid (and/or acetic anhydride and/or acetaldehyde) are recovered and unconverted or partially converted materials and halogen-containing components of the reaction medium are recovered for recycle to the reaction zone. The catalyst can also be readily recovered for recycle to the reaction zone if desired.

As hereinbefore indicated, the ethylidene diacetate-forming reaction to which this invention is directed is carried out in the presence of the co-catalyst-promoter system described above.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the nickel and co-catalyst into the reaction system. Thus, typical compounds include the carbonate, oxide, hydroxide, bromide, iodide, chloride, oxyhalide, hydride, lower alkoxide (methoxide) phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of nickel or of the co-catalyst component can be employed, e.g., carbonyls and metal alkyls as well as chelates, association compounds and enol salts. Examples of other complexes include bis-(triphenyl phosphine) nickel dicarbonyl, tricyclopentadienyl trinickel dicarbonyl, tetrakis (triphenyl phosphite) nickel, and corresponding complexes of the other components, such as molybdenum hexacarbonyl and tungsten hexacarbonyl.

Included among the catalyst components listed above are complexes of the metal co-catalyst components with organic promoter ligands derived from the organic promoters hereinafter described. Particularly preferred are the elemental forms, compounds which are iodides, and organic salts, e.g., salts of the monocarboxylic acid corresponding to the anhydride being used. It will be understood that the foregoing compounds and complexes are merely illustrative of suitable forms of the nickel and co-catalyst components and are not intended to be limiting.

The specified co-catalyst components employed may contain impurities normally associated with the commercially available metal or metal compounds and need not be purified any further.

The promoter is, as said, an organo-phosphorus or nitrogen compound wherein P and N are trivalent. The organo-phosphorus promoter is preferably a phosphine, e.g., a phosphine of the

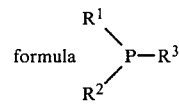

formula wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine,8-quinolinol, 1-methylpyrrolidinone, 2-imidazolidone, N,N-dimethylacetamide, dicyclohexylacetamide, dicyclohexyl-methylamine, 2,6-diaminopyridine, 2-quinolinol, N,N-diethyltoluamide, and imidazole.

Although generally the organic promoter is added separately to the catalyst system, it is also possible to add it as a complex with any of the co-catalyst metals, such as bis(triphenyl phosphine) nickel dicarbonyl and tetrakis (triphenyl phosphite) nickel. Both free organic promoters and complexes promoters can also be used. Indeed, when a complex of the organic promoter and the co-catalyst metal is used, free organic promoter can also be added.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 mol per 10 to 10,000 mols of methyl acetate or dimethyl ether, preferably 1 mol per 100 to 5,000 mols of methyl acetate or dimethyl ether and most preferably 1 mol per 500 to 1,000 mols of methyl acetate or dimethyl ether.

The ratio of nickel to the other co-catalyst component can vary. Typically, it is one mol of the nickel per 0.01 to 100 mols of the other co-catalyst component, preferably the nickel component is used in the amount of 1 mol per 0.1 to 20 mols, most preferably 1 mol per 1 to 10 mols of the other co-catalyst component.

The quantity of organic promoter can also vary widely but typically it is used in the amount of 1 mol per 0.1 to 10 mols of the co-catalyst components, preferably 1 mol per 0.5 to 5 mols, most preferably 1 mol per 1 to 5 mols of the co-catalyst component.

A particular embodiment of the catalyst comprising the molybdenum-nickel or tungsten-nickel co-catalyst component, the organic promoter component and the iodide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the

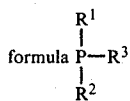

formula $\begin{array}{c} R^1 \\ | \\ P-R^3 \\ | \\ R^2 \end{array}$ as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of ethylidene diacetate, the other organic components being recycled and, in a liquid-phase reaction, a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst components; their concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention.

EXAMPLE 1

A pressure vessel made of Hastelloy-C is charged with a mixture containing 25 weight percent methyl acetate, 60 weight percent methyl iodide, 1.4 weight percent bis-triphenylphosphine nickel dicarbonyl, 5.4 weight percent triphenylphosphine, 2.8 weight percent molybdenum hexacarbonyl, and 5.4 weight percent acetic acid. The vessel is swept out with argon and pressured to 300 psig with carbon monoxide and up to 600 psig hydrogen. The vessel is heated to 140° C. with stirring. At this temperature the pressure is 900 psig. The vessel is pressured up to 1200 psig using equal amounts of carbon monoxide and hydrogen and is maintained at this pressure by recharging equal amounts of carbon monoxide and H$_2$ when needed. After 8 hours reaction time, G. C. analysis of the reaction mixture shows it to contain 9.2 weight percent ethylidene diacetate.

EXAMPLE 2

Example 1 is repeated with the exception that molybdenum hexacarbonyl is replaced with tungsten hexacarbonyl. Similar results were obtained after a reaction time of 8 hours.

EXAMPLE 3

Example 1 is repeated with the exception that molybdenum hexacarbonyl is replaced with chromium hexacarbonyl. After a reaction time of 8 hours, G. C. analysis of the reaction mixture showed only traces of ethylidene diacetate.

EXAMPLE 4

When Example 1 is repeated but with 0.5 weight percent nickel hexacarbonyl and 4 weight percent imidazole, the reaction mixture contains 8 weight percent ethylidene diacetate.

What is claimed is:

1. A process for the preparation of ethylidene diacetate which comprises reacting methyl acetate and/or dimethyl ether under anhydrous conditions with hydrogen and carbon monoxide in the presence of a molybdenum-nickel co-catalyst or a tungsten-nickel co-catalyst, in the presence of an iodide and in the presence as a promoter of an organo-phosphorus compound or an organo-nitrogen compound wherein the phosphorus and nitrogen are trivalent.

2. A process as defined in claim 1, wherein the co-catalyst is molybdenum-nickel.

3. A process as defined in claim 1, wherein the promoter is a phosphine.

4. A process as defined in claim 3, wherein the co-catalyst is molybdenum-nickel and the promoter is a phosphine.

* * * * *